United States Patent [19]

Mayfield

[11] 4,347,845
[45] Sep. 7, 1982

[54] HOOK INSERTER DEVICE

[76] Inventor: Jack K. Mayfield, 12 Evergreen Rd., St. Paul, Minn. 55110

[21] Appl. No.: 246,296

[22] Filed: Mar. 23, 1981

[51] Int. Cl.³ .................. A61B 17/00; A61F 5/04; A61B 17/18
[52] U.S. Cl. ........................... 128/303 R; 128/92 E; 128/92 EB; 128/92 EC
[58] Field of Search .......... 128/92 E, 92 EA, 92 EB, 128/92 EC, 92 ED, 303.19, 346, 303 R

[56] References Cited

U.S. PATENT DOCUMENTS

| | | | |
|---|---|---|---|
| 306,491 | 10/1884 | Jackman | 128/92 E |
| 954,073 | 4/1910 | Bender | 128/92 E |
| 3,036,482 | 5/1962 | Kenworthy et al. | 128/92 EC |
| 3,604,487 | 9/1971 | Gilbert | 128/303 R |
| 3,955,568 | 5/1976 | Neufeld | 128/92 E |
| 4,269,178 | 5/1981 | Keene | 128/92 EA |
| 4,306,550 | 12/1981 | Forte | 128/92 E |

Primary Examiner—Kyle L. Howell
Assistant Examiner—C. W. Shedd
Attorney, Agent, or Firm—Williamson, Bains, Moore & Hansen

[57] ABSTRACT

A hook inserter device is used for positioning a distraction hook for spinal distraction systems in the treatment of spinal deformities and fractures. The hook inserter device comprises an elongate bar including a handle portion and a hook mounting portion, the latter being of reduced cross-sectional size to permit a distraction hook to be mounted thereon. A positioning member on the bar prevents rotation of the distraction hook during application of the hook to the spine. A retaining member on the bar engages and holds the distraction hook on the mounting portion during placement of the hook but permits ready release thereof after placement of the hook.

4 Claims, 4 Drawing Figures

U.S. Patent    Sep. 7, 1982    4,347,845
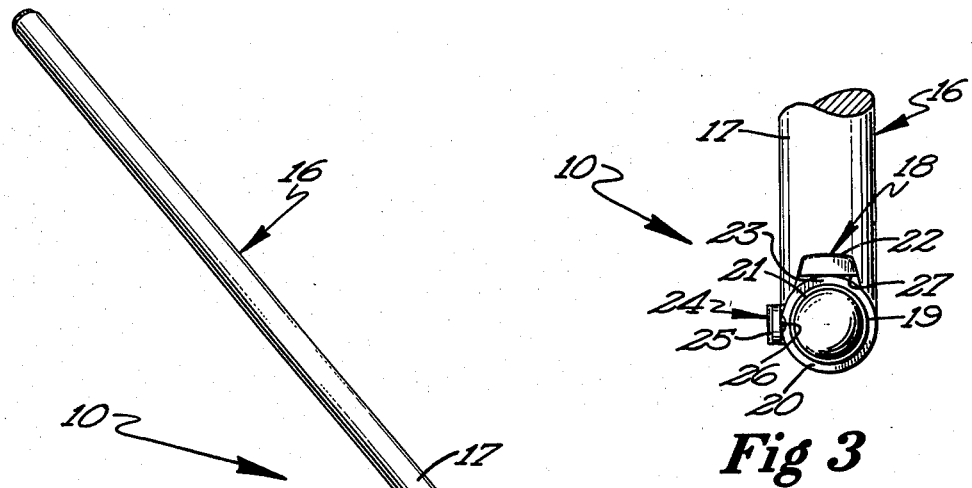
Fig 3
Fig 1
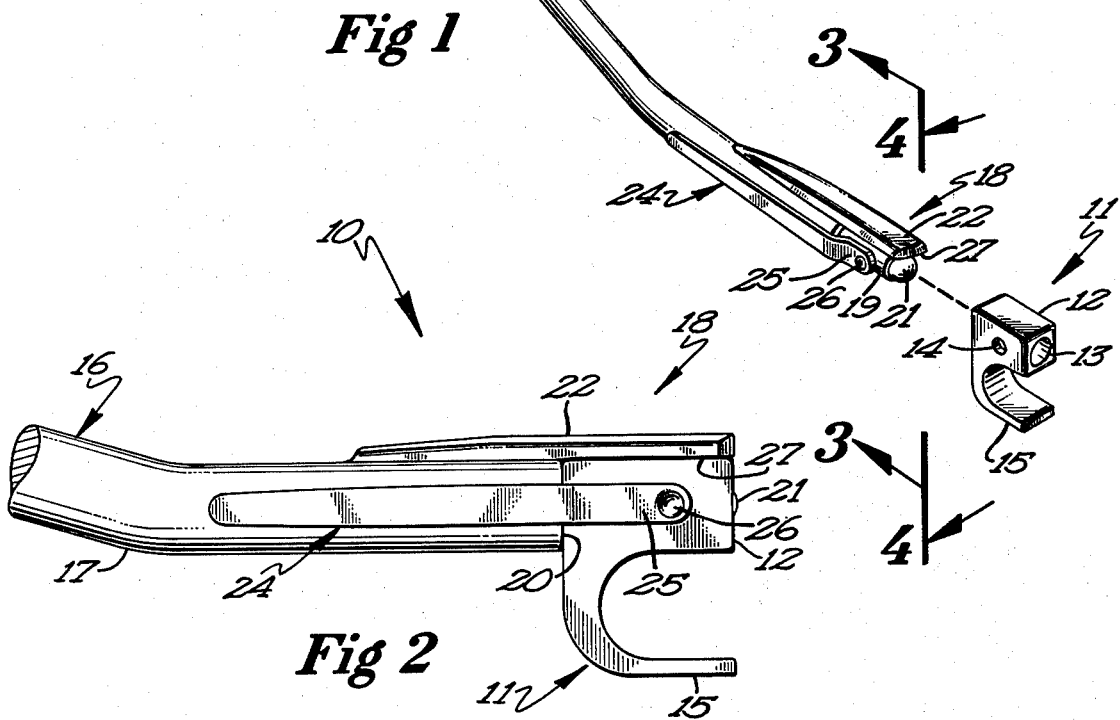
Fig 2
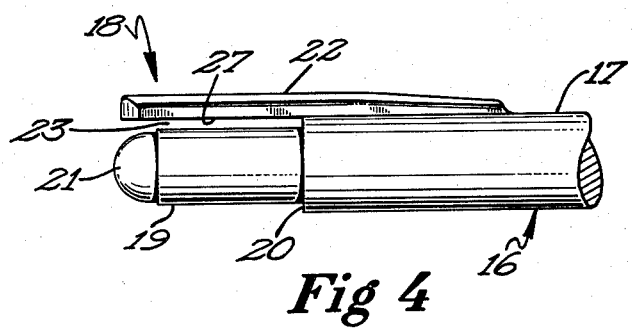
Fig 4

HOOK INSERTER DEVICE

SUMMARY OF THE INVENTION

This invention relates to a device for inserting a distraction hook used in spinal distraction systems.

A method and instruments for treating spinal deformities, particularly, scoliosis, was developed by Paul R. Harrington, M.D., in which a distraction or compression force is applied to the spine by a distraction or a compression rod. The distraction or compression force is transmitted to the spine from the rod by distraction hooks which are placed between selected vertebrae. This procedure is now known as the Harrington Distraction System.

In this procedure, the distraction hook has heretofore been usually manually positioned between the vertebrae and each hook is then forceably driven into place through the use of a mallet and driver tool. The distraction hook tends to rotate as force is applied thereto and special holer forceps are sometimes used to hold a hook during insertion thereof. The conventional driver tool is of elongate, straight configuration and must be applied at an angle to the hook during insertion of the latter. Because of the limited space involved in this procedure, it is difficult to properly position the conventional driver tool during the insertion of the hook.

It is therefore a general object of this invention to provide a novel hook holder device for use in spinal distraction systems which firmly and non-rotatably hold the distraction hook in place during the insertion thereof but permits ready release of the hook after insertion.

Another object of this invention is to provide a novel distraction hook holder device which is of angled configuration to permit the device to be effectively used in confined spaces.

These and other objects and advantages of this invention will more fully appear from the following description made in connection with the accompanying drawings, wherein like reference characters refer to the same or similar parts throughout the several views.

FIGURES OF THE DRAWINGS

FIG. 1 is an exploded perspective view illustrating the novel holder device and a distraction hook used therewith;

FIG. 2 is a side elevational view of one end portion of the holder device with a distraction hook mounted thereon;

FIG. 3 is an end elevational view of the holder device taken approximately along line 3—3 of FIG. 1 and looking in the direction of the arrows; and FIG. 4 is a side elevational view of a portion of the holder device taken approximately along line 4—4 of FIG. 1 and looking in the direction of the arrows.

DESCRIPTION OF THE PREFERRED EMBODIMENT OF THE INVENTION

Referring now to the drawings and more particularly to FIG. 1, it will be seen that one embodiment of the novel hook inserter device, designated generally by the reference numeral 10 is thereshown. The inserter device 10 is used to positively and non-rotatably hold a standard distraction hook 11 during insertion of the latter in a spinal distraction system. In spinal distraction systems, a distraction or compression force is applied to the spine in treatment of spinal deformities, fractures, and in spinal reconstructive surgery. In spinal distraction systems, each hook 11 is positioned between a pair of vertebrae and a distraction rod or a compression rod will extend through the axial opening 13 in the hub 12 of the hook. The distraction bar and compression bar serve to impart sufficient force to correct defectively curved spines. In the conventional procedure, the hook portion 15 of each hook 11 is forced between a selected pair of vertebrae by means of a straight driver tool, the driver tool being driven by a mallet. In this procedure, the surgeon manually grips and holds the hook during insertion and in some instances uses a special holder forceps which engage in the transverse opening 14 in the hub of the hook.

During insertion, the hook tends to rotate and it is often difficult to position and hold the hook for forceps while simultaneously driving the hook into its inserted position with a conventional driver tool. The present holder device serves not only to positively and non-rotatably hold the hook during insertion but permits the surgeon to work in a more confined space then was heretofore possible with a conventional driver tool and holder forceps.

The hook inserter device includes an elongate bar 16 which is formed of a suitable stainless steel material and which includes an elongate handle portion 17 and a hook mounting portion 18. Referring again to FIG. 1, it will be noted that there is an obtuse included angle between the hook mounting portion 18 and the handle portion 17. The hook mounting portion 18 has a reduced end 19 to thereby define the forward facing shoulder 20. The reduced end 19 is adapted to project through the axial opening 13 in the hub 12 of the hook 11. The reduced end 19 terminates in a rounded end portion 21.

An elongate positioning member 22 having a substantially flat lower surface 22a has one end portion thereof secured to the bar 16 and projects forwardly therefrom and is disposed in substantially parallel spaced relation with respect to the reduced end 19. It will also be seen that the outermost end of the positioning member 22 terminates at approximately the same point as the outer tip of the reduced end 19. The space 23 between the reduced end 19 and the planar lower surface 22a of the positioning member is sufficient to permit the hub of the hook 11 to be positioned between the reduced end and the positioning member. When the distraction rod is positioned on the reduced end 19, the positioning member prevents rotation of the hook.

Means are provided for positively holding the hook 11 in mounted relation on the reduced end 19. This means includes an elongate retaining member 24 which is affixed to the mounting portion 18 of the bar 16 and projects forwardly therefrom. It will be seen that the retaining member 24 has an inwardly offset end portion 25 that is provided with an inwardly projecting detent 26. The retaining member 24 is somewhat yieldable so that when the hook 11 is positioned on the reduced end 19, the retaining member will frictionally engage the side of the hook and the detent 26 will engage in the transverse opening 14 of the hook. This frictional interengagement of the retaining member with the hook positively holds the hook during insertion of the hook but permits forceable release of the hook inserter device 10 after the hook has been inserted.

In use, a distraction hook 11 will be positioned upon the reduced end 19 of the hook mounting portion 18 so that the detent 26 engages in the transverse opening 14 in the hub 12. The positioning member 22 will prevent rotation of the hook during insertion of the latter. When the hook is properly positioned between selected vertebra, the end of the handle portion 17 may be struck with a mallet whereby force may be applied to the hook to properly force the hook into a desired position between the selected vertebrae. The angulated configuration of the inserter device facilitates placement of the hook in a very narrow confined space during the insertion procedure. After the hook has been properly placed, the hook is left in situ and the inserter device is forceably removed from engaging relation with the hook. A distraction rod or a compression rod will thereafter be inserted through the axial opening 13 in the hook in accordance with the procedure to be performed.

From the foregoing, it will be seen that I have provided a novel hook inserter device which not only positively and non-rotatably holds a hook in place during insertion of the latter, but permits insertion of a hook in confined spaces during spinal reconstruction surgery.

Thus, it will be seen that I have provided a novel hook inserter device which is not only of simple and inexpensive construction, but one which functions in a more efficient manner than any heretofore known comparable device.

It is anticipated that various changes can be made in the size, shape and construction of the hook inserter device disclosed herein without departing from the spirit and scope of the invention as defined by the following claims.

What is claimed is:

1. A hook inserter device for positioning a hook used in spinal distraction or compressions systems, the hook including a hub having an axial opening therethrough and having a transverse opening through the hub arranged normal to the axial opening therein, a curved hook portion integral with the hub and extending therefrom, said device comprising:

an elongate bar including a handle portion and a hook mounting portion; when being used, said hook mounting portion is inserted into the axial opening in the hub of the distraction hook, positioning means on said bar adjacent said hook mounting portion serves to prevent angular movement of a hook positioned on said mounting portion, and releasable retention means on said bar releasably engaging a hook mounted on said mounting portion to positively but releasably retain the hook in mounting relation on said bar.

2. The hook inserter device as defined in claim 1 wherein the handle portion is disposed in angulated relation with respect to said hook mounting portion.

3. The hook inserter device as defined in claim 1 wherein said hook mounting portion is of reduced cross-sectional size with respect to the cross-sectional size of said bar.

4. The hook inserter device as defined in claim 1 wherein said retention means includes an elongate retaining member having a detent element thereon adapted to engage in the transverse opening of the hook to releasably retain the hook on the hook mounting portion.

* * * * *